(12) United States Patent
Brennan (10) Patent No.: US 8,092,527 B2
(45) Date of Patent: *Jan. 10, 2012

(54) SYSTEM AND METHOD FOR BREAST AUGMENTATION

(76) Inventor: William A. Brennan, Lakeland, FL (US)

( * ) Notice: Subject to any disclaimer, the term of this patent is extended or adjusted under 35 U.S.C. 154(b) by 568 days.

This patent is subject to a terminal disclaimer.

(21) Appl. No.: 11/668,329

(22) Filed: Jan. 29, 2007

(65) Prior Publication Data

US 2007/0123983 A1 May 31, 2007

Related U.S. Application Data

(63) Continuation-in-part of application No. 10/654,156, filed on Sep. 3, 2003, now Pat. No. 7,169,180, and a continuation-in-part of application No. 10/931,899, filed on Sep. 1, 2004.

(51) Int. Cl.
*A61F 2/12* (2006.01)

(52) U.S. Cl. .......................................................... 623/8

(58) Field of Classification Search .................. 623/7–8
See application file for complete search history.

(56) References Cited

U.S. PATENT DOCUMENTS

| | | |
|---|---|---|
| 405,100 A | 6/1889 | Kloppe |
| 833,759 A | 10/1906 | Sourwine |
| 1,155,169 A | 9/1915 | Starkweather |
| 4,199,079 A | 4/1980 | Oloff et al. |
| 4,551,135 A | 11/1985 | Gormann et al. |
| 4,625,722 A | 12/1986 | Murray |
| 4,769,011 A | 9/1988 | Swaniger |
| 4,900,303 A | 2/1990 | Lemelson |
| 4,944,749 A | 7/1990 | Becker |
| 4,955,906 A | 9/1990 | Coggins et al. |
| 4,963,150 A | 10/1990 | Brauman |
| 5,007,940 A * | 4/1991 | Berg .............................. 424/423 |
| 5,022,942 A | 6/1991 | Yan et al. |
| 5,113,846 A | 5/1992 | Hilterbrandt et al. |
| 5,146,933 A | 9/1992 | Boyd |
| 5,147,398 A | 9/1992 | Lynn et al. |
| 5,181,918 A | 1/1993 | Brandhorst et al. |
| 5,246,454 A | 9/1993 | Peterson |
| 5,275,610 A | 1/1994 | Eberbach |
| 5,282,856 A | 2/1994 | Ledergerber |
| 5,336,263 A | 8/1994 | Ersek et al. |
| 5,339,803 A | 8/1994 | Mayzels et al. |
| 5,356,382 A | 10/1994 | Picha et al. |
| 5,425,355 A | 6/1995 | Kulick |
| 5,454,365 A | 10/1995 | Bonutti |
| 5,496,367 A | 3/1996 | Fisher |
| 5,507,808 A | 4/1996 | Becker |
| 5,532,295 A | 7/1996 | Harrison et al. |
| 5,534,023 A * | 7/1996 | Henley .............................. 623/8 |
| 5,549,671 A | 8/1996 | Waybright et al. |
| 5,571,182 A | 11/1996 | Ersek et al. |
| RE35,391 E | 12/1996 | Brauman |
| 5,662,676 A | 9/1997 | Koninckx |
| 5,716,404 A | 2/1998 | Vacanti et al. |
| 5,723,006 A | 3/1998 | Ledergerber |
| 5,738,812 A | 4/1998 | Wild |

(Continued)

*Primary Examiner* — Suzette J Gherbi (74) *Attorney, Agent, or Firm* — Novak Druce + Quigg LLP (57) ABSTRACT

A system for cosmetic augmentation includes a plurality of microballoons. An injector can be provided for injecting microballoons into a subcutaneous pocket at a cosmetic site through an incision. A method for performing cosmetic augmentation surgery and microballoons for use in the method are also disclosed.

13 Claims, 8 Drawing Sheets

U.S. PATENT DOCUMENTS

| | | | |
|---|---|---|---|
| 5,769,849 A | 6/1998 | Eggers | |
| 5,772,665 A | 6/1998 | Glad et al. | |
| 5,792,478 A | 8/1998 | Lawin et al. | |
| 5,871,497 A | 2/1999 | Young | |
| 5,922,025 A | 7/1999 | Hubbard | |
| 5,957,900 A | 9/1999 | Ouchi | |
| 6,001,120 A | 12/1999 | Levin | |
| 6,030,406 A | 2/2000 | Davis et al. | |
| 6,083,264 A | 7/2000 | Wood et al. | |
| 6,099,565 A | 8/2000 | Sakura, Jr. | |
| 6,183,514 B1 | 2/2001 | Becker | |
| 6,187,043 B1 * | 2/2001 | Ledergerber | 623/8 |
| 6,214,331 B1 | 4/2001 | Vanderhoff et al. | |
| 6,261,323 B1 | 7/2001 | Neto | |
| 6,290,674 B1 | 9/2001 | Roue et al. | |
| 6,309,395 B1 | 10/2001 | Smith et al. | |
| 6,335,028 B1 | 1/2002 | Vogel et al. | |
| 6,387,133 B1 | 5/2002 | Perouse | |
| 6,432,437 B1 | 8/2002 | Hubbard | |
| 6,464,726 B1 | 10/2002 | Heljenek | |
| 6,495,164 B1 | 12/2002 | Ramstack et al. | |
| 6,514,248 B1 | 2/2003 | Eggers et al. | |
| 6,537,574 B1 | 3/2003 | Hubbard | |
| 6,544,287 B1 | 4/2003 | Johnson et al. | |
| 6,554,803 B1 | 4/2003 | Ashman | |
| 6,558,612 B1 | 5/2003 | Hubbard | |
| 6,932,840 B1 | 8/2005 | Bretz | |
| 7,137,995 B2 | 11/2006 | Studin | |
| 7,846,205 B2 * | 12/2010 | Brennan | 623/8 |

* cited by examiner

SYSTEM AND METHOD FOR BREAST AUGMENTATION

CROSS-REFERENCE TO RELATED APPLICATIONS

This application is a continuation in part of U.S. patent application Ser. No. 10/654,156, filed Sep. 3, 2003, now U.S. Pat. No. 7,169,180, and U.S. patent application Ser. No. 10/931,899, filed Sep. 1, 2004, both of which are incorporated herein by reference in their entirety.

FIELD OF THE INVENTION

This invention relates generally to surgical systems and methods, and more particularly to systems and methods for performing breast augmentation surgery.

BACKGROUND OF THE INVENTION

Breast augmentation surgery is a cosmetic procedure in which a foreign substance is placed into or under the breast to alter the size and/or shape of the breasts. Breast augmentation surgery has been performed for many years according to many different procedures. Generally, these procedures have centered on the use of a single large sack comprised of a silicone elastomer shell that is filled with a silicone gel or saline solution to give the implant a more natural appearance and feel when implanted into the patient. Although this procedure is considered to be generally safer for the patient than prior procedures, it does have some associated complications. All implants can rupture, deflate or leak. Silicone-filled implants will thereby release this foreign substance into the body. Saline-filled implants are considered preferable in that breakage will release only a sterile saline solution into the body. There is concern, however, that the saline-filled implants could support the growth of fungus and certain bacteria. Rupture or leakage would then release these potentially harmful organisms into the patient's body.

A significant complication that exists with both silicone-filled and saline-filled implants is that of capsular contracture. This is a condition in which abnormal scar tissue forms around the implant, resulting in a hard capsule that is abnormal in appearance and can be painful for the patient. It is a chronic condition for which there are few effective treatments that do not require additional surgery.

SUMMARY OF THE INVENTION

A system for breast augmentation comprises a plurality of microballoons. An injector is provided for injecting the microballoons into a breast through an incision in the breast. The microballoons have a first dimension when held by the injector and a second, larger dimension when in the breast.

The microballoons can comprise a flexible, substantially spherical shell defining an open interior. The open interior is filled with a sterile material such as silicone gel or saline solution. The flexible shell can be made of plastic or silicone. In a preferred embodiment, the microballoons have a diameter or largest dimension of between about 1 and about 50 mm. In another aspect, the microballoons have a diameter or largest dimension of between about 3 and about 30 mm. In still another aspect of the invention, the microballoons have a diameter or largest dimension of between about 5 and about 20 mm.

The injector can be any suitable device for holding a microballoon in a first, compressed dimension and then releasing the microballoon into the breast. The microballoon will expand in the breast to the second, expanded dimension. It is also possible to fill or partially fill the microballoons after they have been placed into the breast by appropriate means such as valves or injection by syringe.

In one aspect, the injector comprises a compression chamber for holding the microballoons in the first, compressed dimension. Structure can be provided for forcing the microballoon into the compression chamber. This structure can be vacuum structure. The vacuum structure can comprise an aperture for drawing a sufficient vacuum in the compression chamber to force the microballoon into the compression chamber. A funnel or other suitable structure can be provided for directing microballoons into the compression chamber under the force of the vacuum.

The compression chamber can have an open end and releasing structure can be provided for forcing the microballoon through the open end. The releasing structure can comprise a plunger moveable through the compression chamber. The injector can have an elongated tubular member that is closed at a first end and has an opening at a second end that defines the open end. The tubular member has an open interior defining, at least in part, the compression chamber. The plunger can comprise a piston and an actuating structure. The piston is slidable within the compression chamber and the actuating structure extends through an aperture in the first end. Movement of the actuating structure through the aperture will cause the plunger to move through the compression chamber to force the microballoon through the open end.

A tissue dissector can be provided with an elongated main body portion having a proximal end and a distal end. A pair of dissecting arms have first and second ends. The first ends are pivotally mounted to the distal end of the elongated main body portion. The dissecting arms have a first pivotal position in which the dissecting arms are substantially juxtaposed and a second pivotal position in which the dissecting arms are separated. A flexible dissecting member is connected between substantially the second ends of the dissecting arms. The dissecting member is in an extended, dissecting position when the dissecting arms are in the second pivotal position. Actuating structure is provided for moving the dissecting arms between at least the first and second pivotal positions.

Tensioning structure can be provided for applying pressure to the flexible dissecting member at a position between the dissecting arms. The tensioning structure can extend through the main body portion. In one aspect, the tensioning structure is an elongated tensioning rod. Gripping structure can be provided for gripping and operating the tensioning rod.

The actuating structure for the dissecting arms can be any suitable actuating structure. In one aspect, the actuating structure is a squeeze grip. Operation of the squeeze grip moves the dissecting arms from the first pivotal position to the second pivotal position. Biasing structure can be provided to return the dissecting arms to the first pivotal position.

A method for performing breast augmentation surgery can include the step of making an incision under the breast. A subcutaneous pocket is made under the breast. A tissue dissector can be inserted through the incision and used to make the subcutaneous pocket under the breast. A plurality of microballoons are then placed into the subcutaneous pocket. A compressed microballoon can be provided with a microballoon injector. The injector holds the microballoon in the compressed condition and permits insertion into the subcutaneous pocket through the incision. The injector is inserted through the incision and the microballoon is released, whereby the microballoon assumes a second, larger dimension when in the subcutaneous pocket. The procedure is repeated until a plurality of the microballoons have been released into the subcutaneous pocket.

BRIEF DESCRIPTION OF THE DRAWINGS

There are shown in the drawings embodiments which are presently preferred, it being understood, however, that the invention is not limited to the precise arrangements and instrumentalities shown, wherein.

DETAILED DESCRIPTION OF THE PREFERRED EMBODIMENTS

Figure 1:
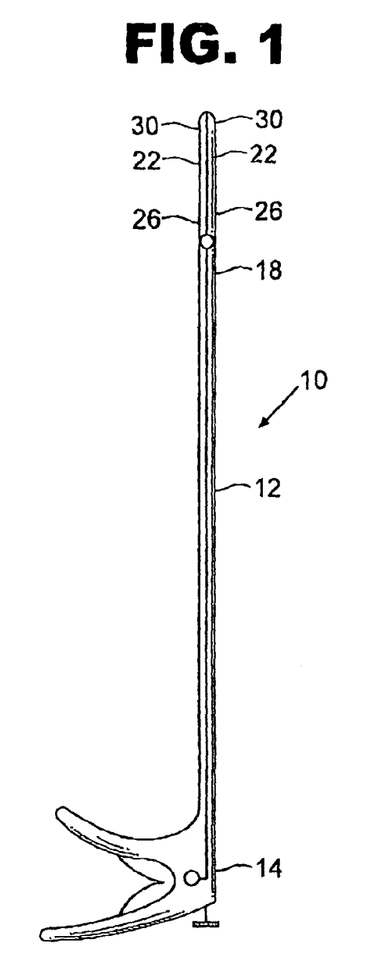
FIG. 1 is a side elevation of a tissue dissector according to the invention in a first configuration.
Figure 2:
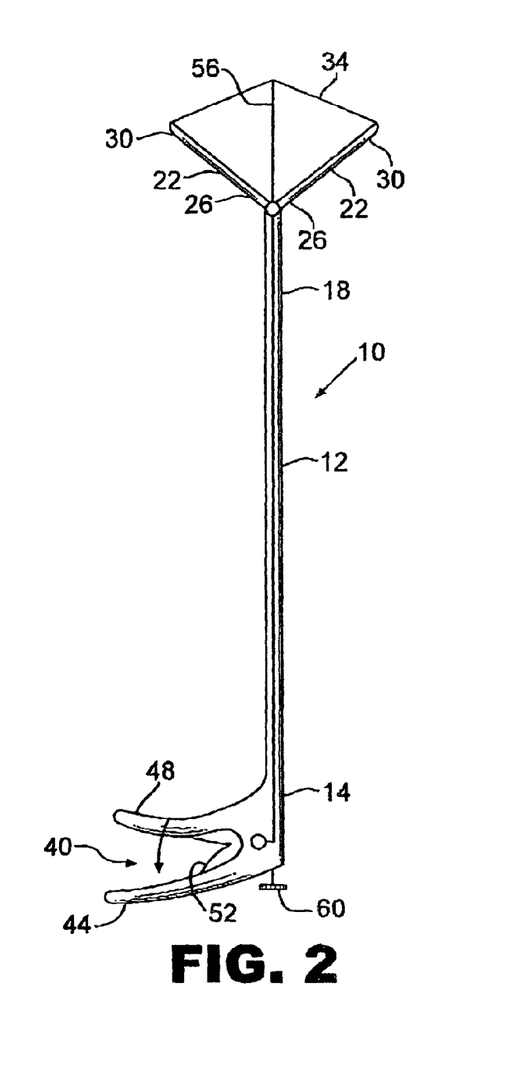
FIG. 2 is a side elevation in a second configuration.

There is shown in FIGS. 1-2 a tissue dissector 10 according to the invention. The tissue dissector 10 has an elongated main body portion 12 having a proximal end 14 and a distal end 18. A pair of dissecting arms 22 have first ends 26 and second ends 30. The first ends 26 are pivotally mounted to the distal end 18 of the elongated main body portion 12. The dissecting arms 22 have a first pivotal position (FIG. 1) in which the dissecting arms 22 are substantially juxtaposed. In a second pivotal position shown in FIG. 2, the dissecting arms 22 are separated.

A flexible dissecting member such as cable 34 is connected substantially between the second ends 30 of the dissecting arms 22. The dissecting cable 34 is in a substantially taut and extended dissecting position when the dissecting arms 22 are in the second pivotal position shown in FIG. 2.

Actuating structure can be provided for moving the dissecting arms 22 between at least the first and second pivotal positions. The actuating structure can be a squeeze grip 40 having a handle 44 and a movable grip lever 48. Suitable linkage is provided such that movement of the grip lever 48 in the direction shown by the arrow will cause the dissecting arms 22 to move from the first pivotal position to the second pivotal position. A biasing such as spring 52 can be provided to cause the dissecting arms 22 to return to the first pivotal position when the grip lever 48 is released. Other actuating structure is possible.

Movement of the dissecting arms 22 to the second pivotal position will cause the cable 34 to extend. The dissecting cable 34 can be placed under tension by appropriate tensioning structure. In one aspect, a moveable tensioning rod 56 is provided to contact the dissecting cable 34 and place the dissecting cable 34 under tension. The tensioning rod 56 can be elongated and positioned through a suitable channel in the elongated main body portion 12. Gripping structure such as end 60 can be provided with which to manipulate the tensioning rod 56 to the extended position shown in FIG. 2 where the dissecting cable 34 is placed under tension. The tensioning rod 56 can be retracted by movement of the end 60 away from the proximal end 14. Other tensioning structure is possible.

The tissue dissector is used to form a subcutaneous pocket under the breast. The dissecting arms 22 are kept in the first pivotal position shown in FIG. 1 to insert the distal end 18 of the tissue dissector 10 through an incision under the breast. Only a small incision need be made due to the small cross-sectional area of the tissue dissector 10 when in the first pivotal position shown in FIG. 1. The actuating structure is then operated to open the dissecting arms 22 to the second pivotal position shown in FIG. 2. The tensioning structure is operated by movement of the tensioning rod 56 to the extended position, such that the dissecting cable 34 is substantially taut. The dissecting cable 34 is of a dimension such that, when taut, it will cut tissue under the breast to form a subcutaneous pocket.

The open configuration shown in FIG. 2, while in the breast, permits the rapid formation of a subcutaneous pocket under the breast, with minimal motion of the tissue dissector. The dissecting arms 22 are then returned to the first pivotal position by a release of the grip lever 48 and return of the tensioning rod 56 to the initial positions, such that the tissue dissector 10 can easily be removed through the incision.

Figure 3A:
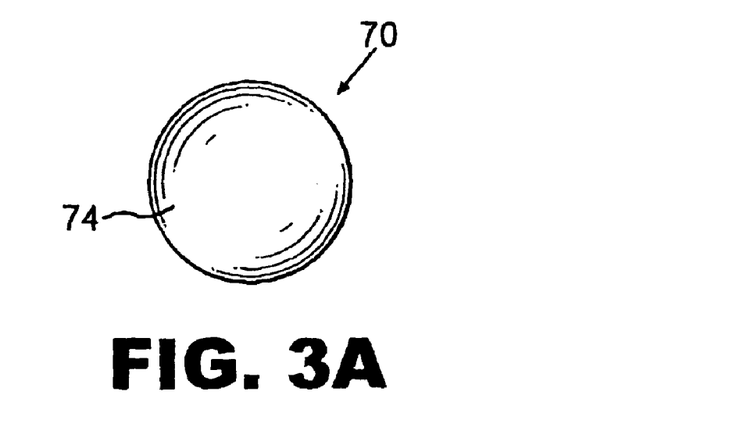
FIG. 3(A) is a side elevation of a microballoon according to the invention.
Figure 3B:
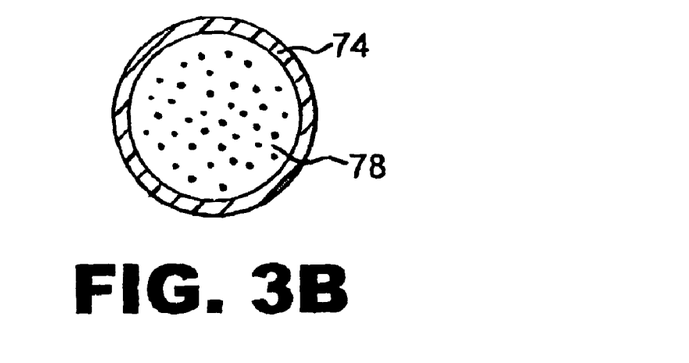
FIG. 3(B) is a cross-section of a microballoon according to the invention.

There is shown in FIGS. 3A-B, a microballoon 70 according to the invention. The microballoon 70 has a flexible exterior shell 74 defining an open interior that is filled by a material 78 that is either a fluid, a gel, or a gas. The microballoon 70 is thereby elastically deformable due to the flexible shell 74 and filled interior. The flexible shell 74 can be made from several suitable materials. In one embodiment, the flexible shell is made of silicone. Other polymeric materials can be used. The filling material 78 can be any suitable material, such as saline solution, hydrogen gas or air, or silicone gel. Additionally, solid or semi-solid microballoons 70 are possible as long as they are elastically deformable.

The microballoons 70 are preferably spherical in shape, but can also be non-spherical. According to the invention, a plurality of the microballoons 70 are implanted into or under each breast and, accordingly, the dimensions of the microballoons 70 are much smaller than current breast implants. In a preferred embodiment, the microballoons have a diameter or largest dimension of between about 1 and about 50 mm. In another aspect, the microballoons have a diameter or largest dimension of between about 3 and about 30 mm. In still another aspect of the invention, the microballoons have a diameter or largest dimension of between about 5 and about 20 mm, and can be between 10-15 mm.

Figure 12:
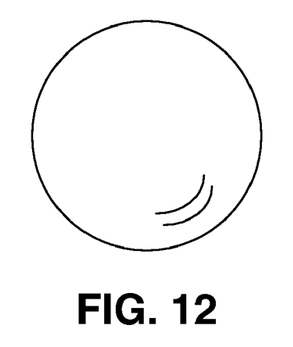
FIG. 12 is a side elevation of an embodiment of a microballoon according to the invention.
Figure 13:
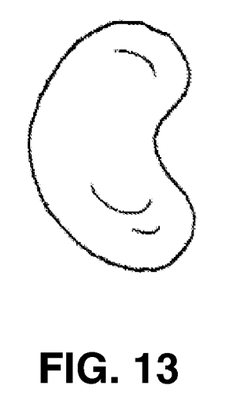
FIG. 13 is a side elevation of another embodiment of a microballoon according to the invention.
Figure 14:
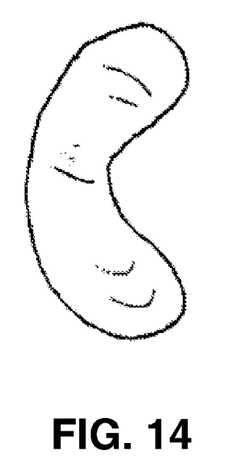
FIG. 14 is a side elevation of another embodiment of a microballoon according to the invention.
Figure 15:
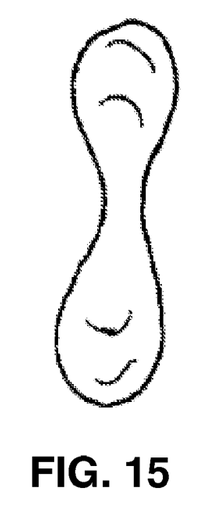
FIG. 15 is a side elevation of another embodiment of a microballoon according to the invention.
Figure 16:
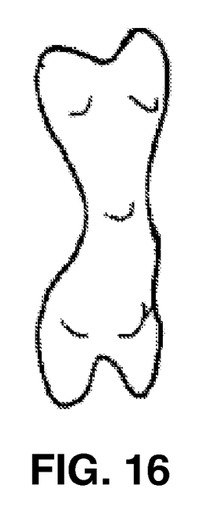
FIG. 16 is a side elevation of another embodiment of a microballoon according to the invention.

The microballoons are mostly spherical and may be either completely filled or partially filled. The microballoons can be comprised of an outer shell of a synthetic polymer, possibly silicone based. The microballoons are also comprised of an inner compartment of a gas, liquid, gel, which occupies a volume of the interior in a range that will produce microballoons filled to various fractions of completely full. In one embodiment, the microballoon is 75% filled relative to volumetric capacity (FIG. 13), in another it is 50% filled (FIG. 14) and in yet another it is 20% filled (FIG. 15), and in another it is 10% (FIG. 16). There are also microballoons that may be 100% filled (FIG. 12). In the microballoons that are less that 100% filled, the outer shell will take on a mostly non spherical configuration, such as plate like, oblong, dimpled, curved, waved, asymmetric and irregular.

Figure 4:
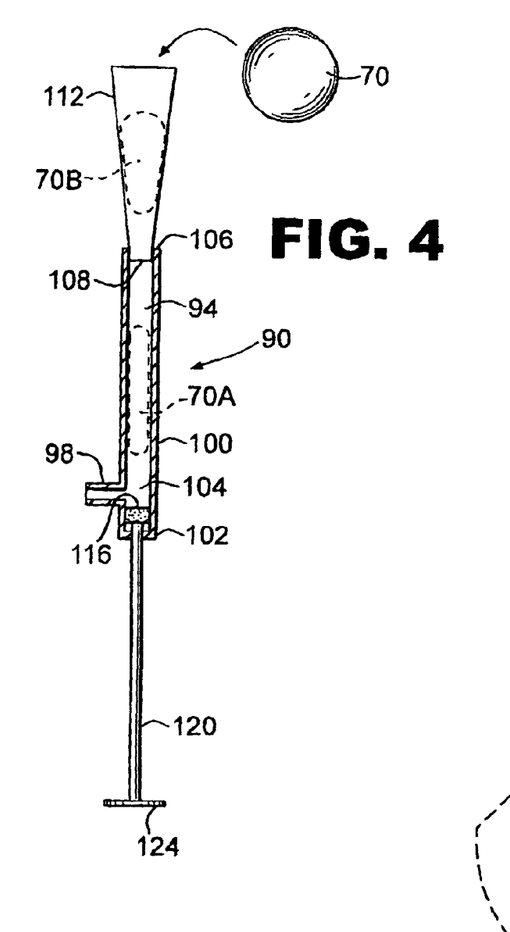
FIG. 4 is a cross-section, partially in phantom, of a microballoon injector according to the invention.
Figure 5:
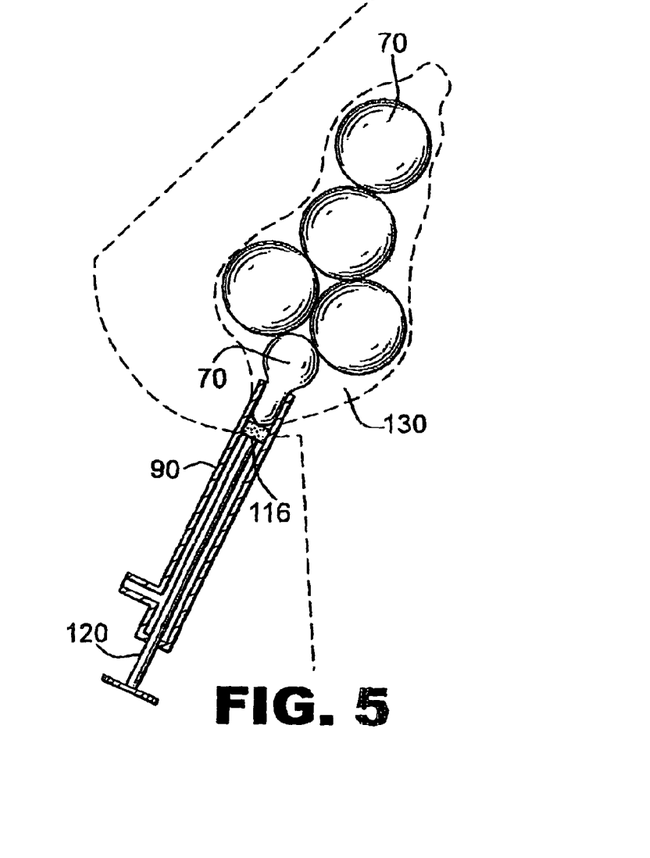
FIG. 5 is a cross-section, partially in phantom, illustrating a breast augmentation procedure according to the invention.
Figures 6, 7:
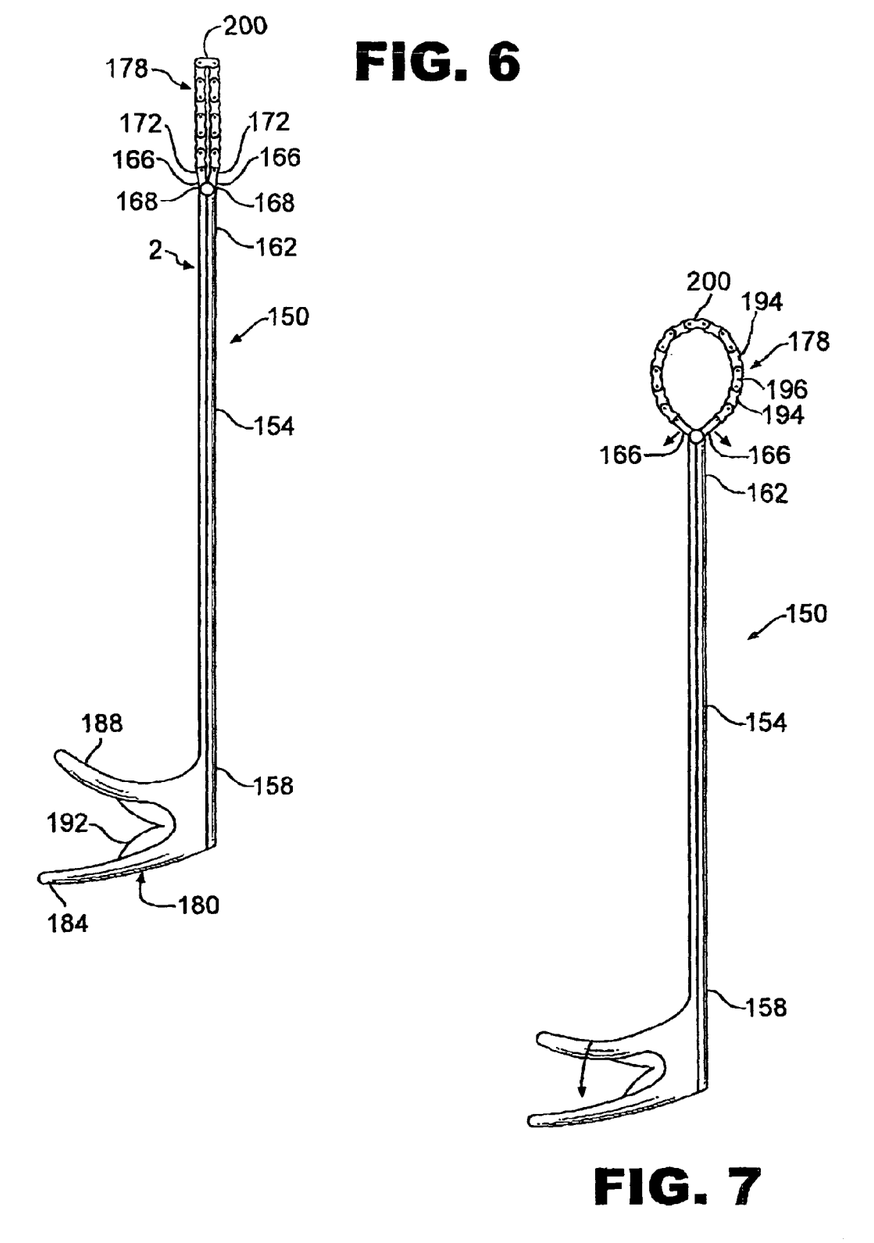
FIG. 6 is a top plan view of an alternative embodiment of a tissue dissector according to the invention, in a first configuration.
FIG. 7 is a top plan view of an alternative embodiment of a tissue dissector according to the invention, in a second configuration.
Figure 8:
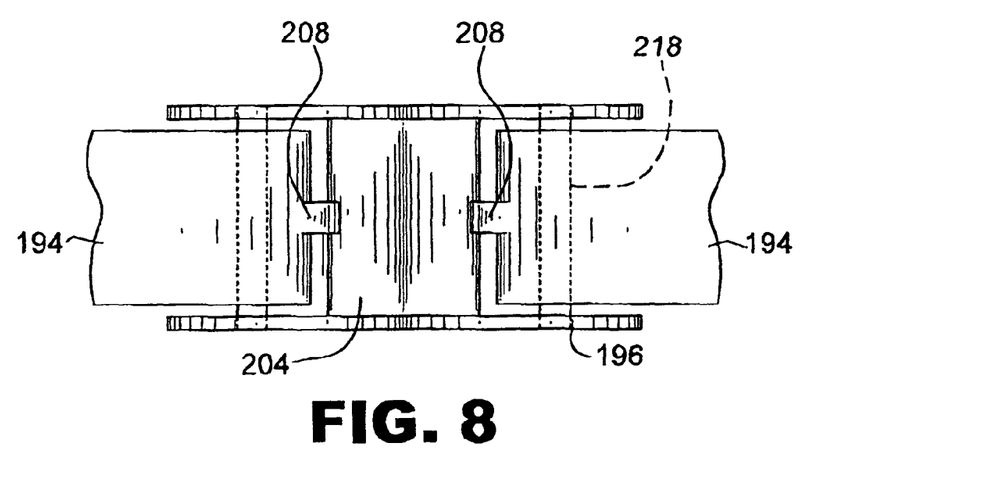
FIG. 8 is a side elevation of a dissecting member, partially in phantom.
Figure 9:
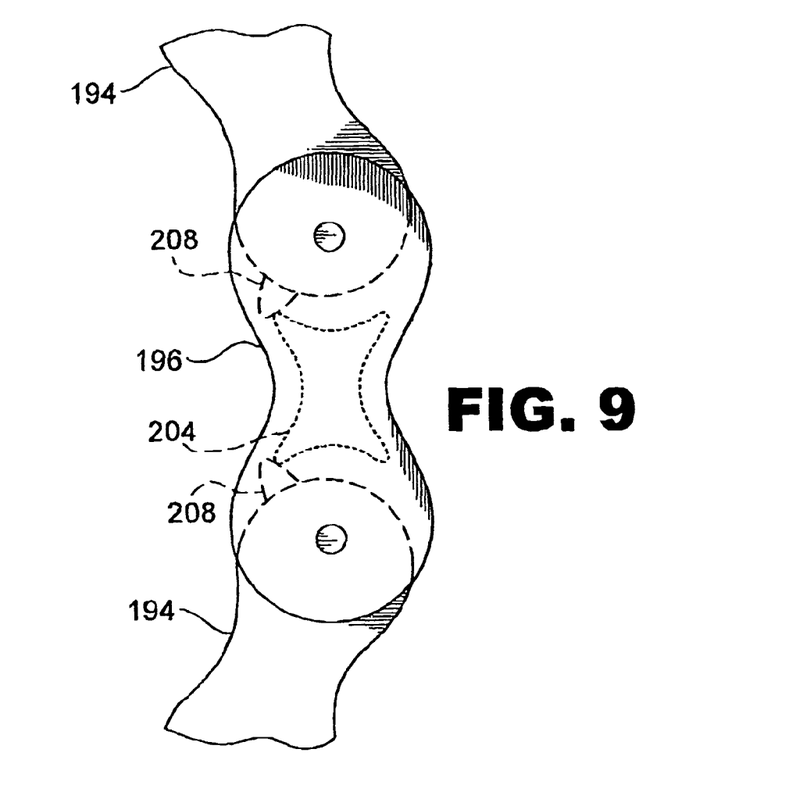
FIG. 9 is a top plan view of a dissecting member, partially in phantom.
Figure 10:
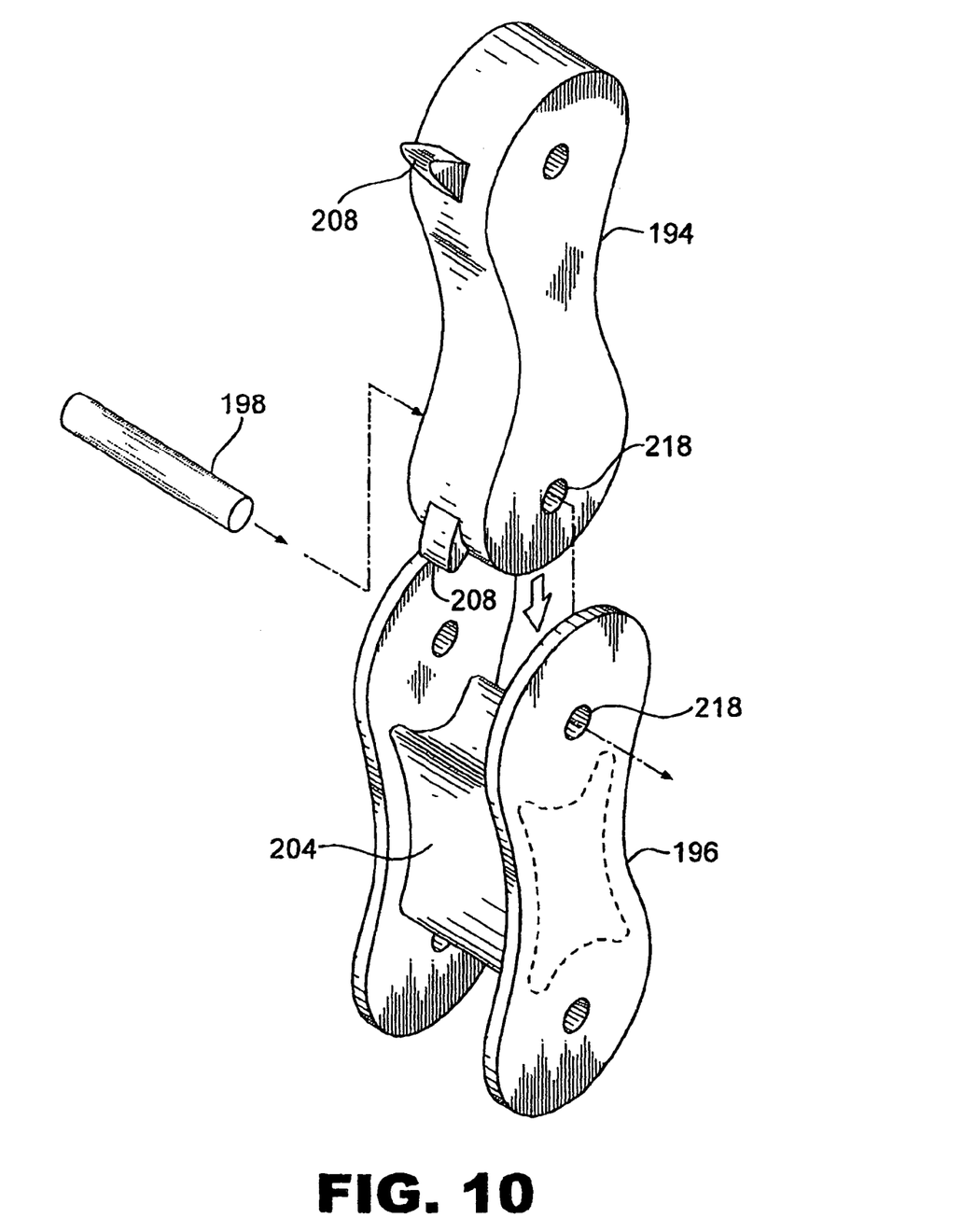
FIG. 10 is an exploded perspective of a portion of a dissecting member, partially in phantom.

An injector assembly for injecting a microballoon into a subcutaneous pocket can include an injector having an elongated delivery portion with a delivery chamber, where the delivery chamber has an outlet. At least one microballoon is positioned in the injector. Structure can be provided for driving the microballoon through the outlet of the delivery chamber into the subcutaneous pocket. In one embodiment, an injector can be used to hold at least one microballoon 70 in a compressed position with a first, compressed dimension, and to release the microballoon when in the breast to permit the microballoon to expand to a second, larger dimension in the subcutaneous pocket. In this manner, the microballoon 70 can be inserted into the subcutaneous pocket through a smaller incision. One such injector 90 is shown in FIGS. 4-5. The structure for holding the microballoon 70 in a first, compressed dimension can be any suitable structure, but in one aspect is a compression chamber 94 into which the microballoon 70 is inserted. The microballoon 70 when inserted in the compression chamber 94 assumes an elongated, deformed shape (indicated by phantom lines 70A in FIG. 4). The extent of compression can vary. In the case of spherical microballoon 70, it is preferable that the microballoon be compressed to 10-90% of the expanded diameter. In one aspect, the microballoon is compressed to about 50% of the expanded diameter.

The injector 90 can be an elongated tubular member having a housing 100 and an open interior 104. The compression chamber 94 can be formed in part by the housing 100. The manner in which the microballoons 70 are loaded into the injector 90 can vary. A manipulator can be used to apply a mechanical force to the microballoons 70 to force them into the compression chamber 94. In another aspect, a vacuum source is applied to a vacuum fitting 98 such that a sufficient force of vacuum is used to draw the microballoons 70 into the compression chamber 94.

Suitable structure can be utilized to guide the microballoons 70 through an opening 108 in the second end 106 of the housing 100. Structure such as detachable funnel 112 can be provided to assist and direct the microballoon 70B (dashed lines in FIG. 4) into the opening 108.

Releasing structure is provided for releasing the microballoon 70 from the injector 90 into the subcutaneous pocket under a breast to permit the balloon to expand in the pocket to the second, expanded dimension. Any suitable structure can be used. In one aspect, a plunger 116 is movable within the open interior 104 of the housing 100. An actuating structure 120 such as an elongated rod can extend through a suitable opening in the first end 102 of housing 100. A head 124 can be provided to facilitate manipulation by hand.

The microballoon is drawn into the injector 90 to the position shown by the microballoon 70A using funnel 112. In this position, the microballoon is in a first, compressed shape. The funnel 112 is then removed. The injector 90 is then inserted through the incision under the breast into the subcutaneous pocket 130 (FIG. 5). The releasing structure such as plunger 116 is then manipulated as by actuating structure 120 to push the microballoon 70 into the subcutaneous pocket 130 as shown in FIG. 5. The microballoon will then expand to the second, expanded dimension.

The number of microballoons 70 that are implanted into the breast or other cosmetic site can vary. At least 3 microballoons are necessary. In one aspect, the number varies from about 3 to about 3000 microballoons. Alternatively, there can be between 3-2000 microballoons. There can be between 3-1000 microballoons. In another aspect, between about 50 and about 300 microballoons are used. The number will depend in part on the size of the patient, the amount of augmentation that is desired, and the shape and size of microballoons 70. The microballoons 70 can be of the same size or different sizes. The invention can be used to perform cosmetic augmentations at a plurality of cosmetic sites. Suitable cosmetic augmentation sites can include the breast, buttock, calf, pectoral area, and upper arm (triceps and biceps). The number of microballoons that are necessary will depend in part on the site of cosmetic augmentation and the volume of the subcutaneous pocket that is to be filled for that cosmetic augmentation.

The plurality of microballoons 70 in the subcutaneous pocket 130 provides for a more natural shape and appearance. Additionally, because the microballoons 70 are free to move slightly within the subcutaneous pocket 130, it is believed that the likelihood of severe scarring will be reduced. Also, the microballoons 70 will more readily conform to the shape of the subcutaneous pocket 130 than does a larger implant.

There is shown in FIGS. 6-10, an alternative embodiment of a tissue dissector according to the invention. The tissue dissector 150 has an elongated main body portion 154, having a proximal end 158 and a distal end 162. A pair of dissecting arms 166 have first ends 168 and second ends 172. The first ends 168 are pivotally mounted to the distal end 162 of the elongated main body portion 154. The dissecting arms 166 have a first pivotal position (FIG. 6) in which the dissecting arms 166 are substantially juxtaposed. In a second pivotal position shown in FIG. 7, the dissecting arms 166 are separated.

A flexible dissecting member 178 is connected substantially between the second ends 172 of the dissecting arms 166. The dissecting member 178 is in an extended dissecting position when the dissecting arms 166 are in the second pivotal position shown in FIG. 2. Actuating structure such as the squeeze grip 180 having a handle 184 and a movable grip lever 188 can be provided. Suitable linkage can be provided such that movement of the grip lever 188 will cause the dissecting arms 166 to move from the first pivotal position to the second pivotal position. A biasing such as spring 192 can be provided to cause the dissecting arms 166 to return to the first pivotal position when the grip lever 188 is released. Other actuating structure is possible.

The dissecting member 178 can be comprised of a number of links 194 connected to junction members 196. The links 194 are engaged to the junction members 196 through appropriate pins 198 or other suitable structure. The pins 198 permit each link 194 to pivot relative to the junction members 196. In this manner, the dissecting member 178 is flexible and can be positioned from the position shown in FIG. 6 to the position shown in FIG. 7. A distal link 200 permits the adjoining links 194 to pivot to the juxtaposed position shown in FIG. 6.

The dissecting member 178 must not flex toward the distal end 162 of the elongated main body portion 154 during the tissue dissection operation. The junction members 196 are constructed so as to restrict inward flexing of the dissecting member 178. The structure to prevent this flexing can take various forms and embodiments. In the embodiments shown in FIGS. 8-10, the junction members 196 are provided with a stop 204. Adjacent links 194 have protrusions 208 which engage the stop 204 to prevent the inward flexing of the dissecting member 178. Similar protrusions 208 and stops 204 can be provided on other links 194 to prevent the inward flexing of the dissecting member 178. Pins 198 or other suitable structure can be provided to pivotally engage the links 194 to the junction members 196. Pins 198 can extend through suitable apertures 218. A distal link 200 is constructed to permit positioning of the flexible member 178 in the juxtaposed and extended positions shown in FIGS. 6-7.

Figure 11:
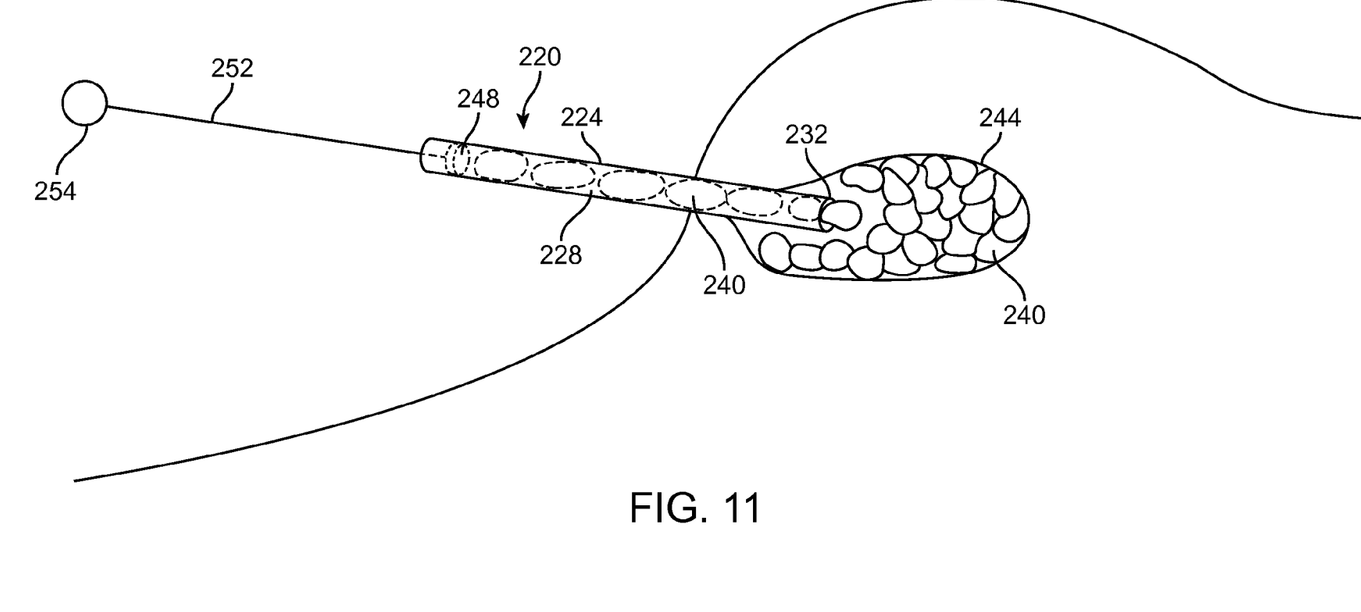
FIG. 11 is a schematic diagram of a microballoon injector according to another embodiment of the invention.

There is shown in FIG. 11 an injector 220 according to an alternative embodiment of the invention. The injector 220 has an elongated delivery portion 224 comprising a delivery chamber 228, the delivery chamber having an outlet 232. The delivery portion 224 can be any suitable shape such as straight, curved or coiled in shape, but should provide for the storage and sequential injection of microballoons. Microballoons 240 are positioned in the injector in the delivery portion 224. Any number of microballoons 240 can be provided in the delivery chamber 228. A single microballoon 240 can be provided, however, to facilitate and speed the injection process between 2-30 or more microballoons 240 are provided in a single injector. Delivery structure is provided for driving the microballoons 240 through the outlet 232 of the delivery chamber into the subcutaneous pocket 244. The delivery structure can be any suitable structure for driving the microballoons 240 through the outlet 232, such as a plunger moveable through the delivery chamber 228 to drive the microballoon through the outlet 232. The plunger can have a piston 248 and an actuating structure 252, which can be an arm with a manual manipulator such as a finger grip 254. The piston 248 is slidable within the delivery chamber and the actuating structure extends through an aperture in the injector, whereby movement of the actuating structure 252 through the aperture will cause the piston 248 to move through the delivery chamber 228 to drive the microballoons through the outlet 232 and into the subcutaneous pocket. The plunger can be removable to permit reuse. Alternatively, the delivery structure can be electronic or motorized. The interior wall of the delivery chamber 228 can be provided with a reduced friction lining, said as graphite, silicone, or polytetrafluoroethylene. The injector assembly including the injector 220 with microballoons 240 positioned in the injector can be provided within a hermetically sealed, sterile packaging container, such that the injector will be ready for use in the operating room.

The components of the invention are preferably made of surgical grade materials such as plastics and stainless steel. Various modifications will be apparent.

This invention can be embodied in other forms without departing from the spirit or essential attributes thereof. Accordingly, reference should be had to the following claims, rather than to the foregoing specification, as indicating the scope of the invention.

I claim:

1. A system for cosmetic augmentation, comprising
at least 3 microballoons adaptable for placement into a previously surgically dissected subcutaneous pocket,
each microballoon comprising a flexible, enclosed shell defining an open interior, said open interior being filled with a filling material,
each microballoon being in contact with at least one other microballoon and no microballoon being in contact with any non-human surface except another microballoon, and no microballoon being connected to any other microballoon or to any human tissue,
said microballoons being at least about 2 mm in diameter, and
said microballoons being elastically deformable.

2. The system of claim 1, further comprising an injector having an elongated delivery portion comprising a delivery chamber, said delivery chamber comprising an outlet, at least one microballoon positioned in said injector, said injector having structure for driving said microballoon through said outlet of said delivery chamber into said subcutaneous pocket.

3. The system of claim 1, wherein said flexible shell comprises a plastic.

4. The system of claim 1, wherein said flexible shell comprises silicone.

5. The system of claim 1, wherein said filling material is a saline solution.

6. The system of claim 1, wherein said filling material is a gas.

7. The system of claim 1, wherein said filling material comprises a silicone gel.

8. The system of claim 1, wherein said microballoon has a largest dimension between about 3 mm and about 30 mm.

9. The system of claim 1, wherein said microballoon has a largest dimension between about 5 mm and about 20 mm.

10. The system of claim 1, wherein said microballoons are between about 10 mm and 15 mm in diameter.

11. The system of claim 2, wherein said injector with said microballoons are encased in a sterile container prior to use.

12. The system of claim 1, wherein said microballoon comprises an outer shell filled with a filling material, the filling material comprising between about 10%-75% of the volumetric capacity of the outer shell.

13. The system of claim 1, comprising between about 3-3000 microballoons.

* * * * *